(12) United States Patent
Kamath et al.

(10) Patent No.: US 7,996,071 B2
(45) Date of Patent: **\*Aug. 9, 2011**

(54) BIOPOTENTIAL SIGNAL SOURCE SEPARATION USING SOURCE IMPEDANCES

(75) Inventors: Apurv Kamath, Solana Beach, CA (US); Darrel Orvin Wagner, Isanti, MN (US); Paul Haefner, Circle Pines, MN (US); Marina Brockway, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 130 days.

This patent is subject to a terminal disclaimer.

(21) Appl. No.: 12/494,768

(22) Filed: Jun. 30, 2009

(65) Prior Publication Data

US 2009/0270750 A1 Oct. 29, 2009

Related U.S. Application Data

(63) Continuation of application No. 10/821,206, filed on Apr. 8, 2004, now Pat. No. 7,555,335.

(60) Provisional application No. 60/462,272, filed on Apr. 11, 2003.

(51) Int. Cl.
*A61B 5/04* (2006.01)

(52) U.S. Cl. ...................................... 600/509
(58) Field of Classification Search ................... 600/509
See application file for complete search history.

(56) References Cited

U.S. PATENT DOCUMENTS

| | | |
|---|---|---|
| RE30,750 E | 9/1981 | Diack et al. |
| 4,562,841 A | 1/1986 | Brockway et al. |
| 4,674,518 A | 6/1987 | Salo |
| 4,784,162 A | 11/1988 | Ricks et al. |
| 4,827,943 A | 5/1989 | Bornn et al. |
| 4,953,551 A | 9/1990 | Mehra et al. |
| 5,036,849 A | 8/1991 | Hauck et al. |
| 5,058,583 A | 10/1991 | Geddes |

(Continued)

FOREIGN PATENT DOCUMENTS

EP 0488512 6/1992

(Continued)

OTHER PUBLICATIONS

Belouchrani et al., *Blind Source Separation Based on Time-Frequency Signal Representations*, IEEE Transactions on Signal Processing, vol. 46, No. 11, pp. 2888-2897, Nov. 1998.

(Continued)

*Primary Examiner* — Eric D. Bertram
(74) *Attorney, Agent, or Firm* — Hollingsworth & Funk, LLC

(57) ABSTRACT

Cardiac methods and devices that separate signals using at least two composite signals acquired at least at two input impedances. A target source impedance may be selected, and a cardiac signal may be separated from composite signals using the selected target source impedance. Medical systems include a cardiac device having a housing that provides amplification circuitry configured to have a first amplifier input impedance and a second amplifier input impedance, such as using two separate circuits or switching between two input impedances. One or more electrode assemblies are coupled to the amplification circuitry. A signal processor is provided in the housing configured to separate a source signal using a first composite signal detected at the first input impedance and a second composite signal detected at the second input impedance. The phase response of the first input amplifier circuit is about equal to that of the second input amplifier circuit.

20 Claims, 15 Drawing Sheets

U.S. PATENT DOCUMENTS

| | | | |
|---|---|---|---|
| 5,113,869 A | 5/1992 | Nappholz et al. |
| 5,117,824 A | 6/1992 | Keimel |
| 5,133,353 A | 7/1992 | Hauser |
| 5,170,784 A | 12/1992 | Ramon et al. |
| 5,176,137 A | 1/1993 | Erickson |
| 5,179,945 A | 1/1993 | Van Hofwegen et al. |
| 5,203,348 A | 4/1993 | Dahl et al. |
| 5,209,229 A | 5/1993 | Gilli |
| 5,230,337 A | 7/1993 | Dahl et al. |
| 5,261,400 A | 11/1993 | Bardy |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,330,505 A | 7/1994 | Cohen |
| 5,331,966 A | 7/1994 | Bennett et al. |
| 5,334,222 A | 8/1994 | Salo et al. |
| 5,342,404 A | 8/1994 | Alt et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,417,714 A | 5/1995 | Levine et al. |
| 5,439,482 A | 8/1995 | Adams et al. |
| 5,441,518 A | 8/1995 | Adams et al. |
| 5,449,652 A | 9/1995 | Swartz |
| 5,464,434 A | 11/1995 | Alt |
| 5,468,254 A | 11/1995 | Hahn et al. |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,556,421 A | 9/1996 | Prutchi et al. |
| 5,601,611 A | 2/1997 | Fayram |
| 5,603,732 A | 2/1997 | Dahl et al. |
| 5,606,969 A | 3/1997 | Butler et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,687,738 A | 11/1997 | Shapiro et al. |
| 5,697,953 A | 12/1997 | Kroll et al. |
| 5,704,365 A * | 1/1998 | Albrecht et al. .............. 600/515 |
| 5,724,984 A | 3/1998 | Arnold et al. |
| 5,827,326 A | 10/1998 | Kroll et al. |
| 5,836,987 A | 11/1998 | Baumann et al. |
| 5,855,593 A | 1/1999 | Olson et al. |
| 5,895,414 A | 4/1999 | Sanchez-Zambrano |
| 5,916,243 A | 6/1999 | KenKnight et al. |
| 5,919,141 A | 7/1999 | Money et al. |
| 5,957,956 A | 9/1999 | Kroll et al. |
| 5,961,446 A | 10/1999 | Beller et al. |
| 5,961,450 A | 10/1999 | Merchant et al. |
| 6,026,320 A | 2/2000 | Carlson et al. |
| 6,044,298 A | 3/2000 | Salo et al. |
| 6,050,940 A | 4/2000 | Braun et al. |
| 6,055,454 A | 4/2000 | Heemels |
| 6,115,628 A | 9/2000 | Stadler et al. |
| 6,122,536 A | 9/2000 | Sun et al. |
| 6,141,581 A | 10/2000 | Olson et al. |
| 6,144,879 A | 11/2000 | Gray |
| 6,148,230 A | 11/2000 | KenKnight |
| 6,198,952 B1 | 3/2001 | Miesel |
| 6,208,888 B1 | 3/2001 | Yonce |
| 6,221,011 B1 | 4/2001 | Bardy |
| 6,227,072 B1 | 5/2001 | Ritchey et al. |
| 6,259,947 B1 | 7/2001 | Olson et al. |
| 6,270,457 B1 | 8/2001 | Bardy |
| 6,277,072 B1 | 8/2001 | Bardy |
| 6,280,380 B1 | 8/2001 | Bardy |
| 6,280,462 B1 | 8/2001 | Hauser et al. |
| 6,285,907 B1 | 9/2001 | Kramer et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,371,922 B1 | 4/2002 | Baumann et al. |
| 6,375,614 B1 | 4/2002 | Braun et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,424,865 B1 | 7/2002 | Ding |
| 6,438,406 B2 | 8/2002 | Yonce |
| 6,438,410 B2 | 8/2002 | Hsu et al. |
| 6,440,066 B1 | 8/2002 | Bardy |
| 6,440,082 B1 | 8/2002 | Joo |
| 6,454,708 B1 | 9/2002 | Ferguson et al. |
| 6,459,929 B1 | 10/2002 | Hopper et al. |
| 6,477,406 B1 | 11/2002 | Turcott |
| 6,480,733 B1 | 11/2002 | Turcott |
| 6,487,443 B2 | 11/2002 | Olson et al. |
| 6,491,639 B1 | 12/2002 | Turcott |
| 6,496,715 B1 | 12/2002 | Lee et al. |
| 6,496,721 B1 | 12/2002 | Yonce |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,597,951 B2 | 7/2003 | Kramer et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,628,986 B1 | 9/2003 | Mouchawar et al. |
| 6,643,540 B2 | 11/2003 | Yonce |
| 6,650,940 B1 | 11/2003 | Zhu et al. |
| 6,684,101 B2 | 1/2004 | Daum |
| 6,701,170 B2 | 3/2004 | Stetson |
| 6,925,325 B2 | 8/2005 | Yonce |
| 6,950,694 B2 | 9/2005 | Yonce |
| 7,236,819 B2 | 6/2007 | Brockway |
| 7,555,335 B2 * | 6/2009 | Kamath et al. ................ 600/509 |
| 7,715,916 B2 | 5/2010 | Haefner |
| 2001/0021813 A1 * | 9/2001 | Yonce .......................... 600/509 |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0085741 A1 | 7/2002 | Shimizu |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107552 A1 | 8/2002 | Gilkerson et al. |
| 2002/0107559 A1 | 8/2002 | Sanders et al. |
| 2002/0120299 A1 | 8/2002 | Ostroff et al. |
| 2002/0136328 A1 | 9/2002 | Shimizu |
| 2002/0147474 A1 | 10/2002 | Morris et al. |
| 2003/0004546 A1 | 1/2003 | Casey |
| 2003/0004552 A1 | 1/2003 | Plombon et al. |

| | | | |
|---|---|---|---|
| 2003/0023175 A1 | 1/2003 | Arzbaecher et al. |
| 2003/0036778 A1 | 2/2003 | Ostroff et al. |
| 2003/0045904 A1 | 3/2003 | Bardy et al. |
| 2003/0060723 A1 | 3/2003 | Joo et al. |
| 2003/0069609 A1 | 4/2003 | Thompson |
| 2003/0088278 A1 | 5/2003 | Bardy et al. |
| 2003/0088279 A1 | 5/2003 | Rissmann et al. |
| 2003/0088280 A1 | 5/2003 | Ostroff et al. |
| 2003/0088281 A1 | 5/2003 | Ostroff et al. |
| 2003/0088282 A1 | 5/2003 | Ostroff et al. |
| 2003/0088283 A1 | 5/2003 | Ostroff et al. |
| 2003/0088286 A1 | 5/2003 | Ostroff et al. |
| 2003/0097153 A1 | 5/2003 | Bardy et al. |
| 2003/0204146 A1 | 10/2003 | Carlson |
| 2003/0212436 A1 | 11/2003 | Brown |
| 2004/0111021 A1 | 6/2004 | Olson |
| 2004/0172066 A1 | 9/2004 | Wagner et al. |
| 2004/0220629 A1 | 11/2004 | Kamath et al. |
| 2004/0220633 A1 | 11/2004 | Wagner et al. |
| 2004/0230129 A1 | 11/2004 | Haefner |
| 2004/0230230 A1 | 11/2004 | Lindstrom |
| 2004/0260522 A1 | 12/2004 | Albera |
| 2005/0010120 A1 | 1/2005 | Jung |
| 2005/0119708 A1 | 6/2005 | Haefner |
| 2005/0240234 A1 | 10/2005 | Joo et al. |
| 2008/0091242 A1 | 4/2008 | Kamath |

FOREIGN PATENT DOCUMENTS

| | | |
|---|---|---|
| WO | WO9217240 | 10/1992 |
| WO | WO9220402 | 11/1992 |
| WO | WO03003905 | 1/2003 |
| WO | WO03020367 | 3/2003 |

OTHER PUBLICATIONS

Comon, *Independent component analysis, A new concept?*, Signal Processing, vol. 36, No. 3, pp. 287-314, Apr. 1994.
Gallois et al., *Multi-Channel Analysis of the EEG Signals and Statistic Particularities for Epileptic Seizure Forecast*, Second Joint EMBS/BMES Conference, pp. 208-215, Oct. 23-26, 2002.
Gradaus et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360, Mar. 2001.
Hartz et al., *New Approach to Defibrillator Insertion*, J. Thoracic Cardiovascular Surgery, vol. 97, pp. 920-922, 1989.
Hyvärinen et al., *Independent Component Analysis: A Tutorial*, Helsinki Univ. of Technology, Apr. 1999.
Kolettis et al., *Submammary Implantation of a Cardioverter-Defibrillator with a Nonthoractomy Lead System*, Am. Heart J., vol. 126, pp. 1222-1223, Nov. 1993.
Krahn, A.D. et al. *Recurrent syncope. Experience with an implantable loop record*. Cardiol. Clin., vol. 15(2), pp. 316-326, May 1997.
Leng et al., *Lead Configuration for Defibrillator Implantation in a Patient with Congenital Heart Disease and a Mechanical Prosthetic Tricuspid Valve*, PACE, vol. 24, No. 8, pp. 1291-1292, Aug. 2001.
Park et al., *Use of an Implantable Cardioverter Defibrillator in an Eight-Month-Old Infant with Ventricular Fibrillation Arising from a Myocardial Fibroma*, PACE, vol. 22, No. 1, pp. 138-139, Jan. 1999.
Rieta et al., *Atrial Activity Extraction Based on Blind Source Separation as an Alternative to QRST Cancellation for Atrial Fibrillation Analysis*, Computers in Cardiology, vol. 27, pp. 69-72, 2000.
Schuder et al., *Experimental Ventricular Defibrillation with an Automatic and Completely Implanted System*, Trans. Am. Soc. Artif. Int. Organs, vol. 16, pp. 207-212, 1970.
Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415, Nov. 1971.
Schuder et al., *Ventricular Defibrillation in the Dog Using Implanted and Partially Implanted Electrode Systems*, Am. J. of Cardiology, vol. 33, pp. 243-247,Feb. 1974.
Smits et al., *Defibrillation Threshold (DFT) Model of a Fully Subcutaneous ICD System*, Europace Supplements, vol. 2, at col. 778, p. B83, Jun. 2001.
Stirbis et al., *Optimizing the Shape of Implanted Artificial Pacemakers*, Kaunas Medical Institute. Translated from Meditsinskaya Tekhnika, No. 6, pp. 25-27, 1986.
Zarzoso et al., *Blind Separation of Independent Sources for Virtually Any Source Probability Density Function*, IEEE Transactions on Signal Processing, vol. 47, No. 9, pp. 2419-2432, Sep. 1999.
Zarzoso et al., *Noninvasive Fetal Electrocardiogram Extraction: Blind Separation Versus Adaptive Noise Cancellation*, IEEE Transactions on Biomedical Engineering, vol. 48, No. 1, pp. 12-18, Jan. 2001.
Notice of Allowance dated Feb. 2, 2007 from U.S. Appl. No. 10/741,814, 5 pages.
Office Action Response dated Nov. 1, 2006 from U.S. Appl. No. 10/741,814, 20 pages.
Office Action dated Aug. 1, 2006 from U.S. Appl. No. 10/741,814, 4 pages.
Office Action Response dated May 5, 2006 from U.S. Appl. No. 10/741,814, 16 pages.
Office Action dated Apr. 5, 2006 from U.S. Appl. No. 10/741,814, 4 pages.
Office Action Response dated May 10, 2010 from U.S. Appl. No. 11/975,040, 6 pages.
Office Action dated Mar. 10, 2010 from U.S. Appl. No. 11/975,040, 6 pages.
Notice of Allowance dated Feb. 25, 2009 from U.S. Appl. No. 10/821,206, 7 pages.
Office Action Response dated Oct. 6, 2008 from U.S. Appl. No. 10/821,206, 15 pages.
Interview Summary dated Sep. 24, 2008 from U.S. Appl. No. 10/821,206, 2 pages.
Office Action dated May 9, 2008 from U.S. Appl. No. 10/821,206, 8 pages.
Office Action Response dated Feb. 11, 2008 from U.S. Appl. No. 10/821,206, 12 pages.
Office Action dated Jan. 10, 2008 from U.S. Appl. No. 10/821,206, 8 pages.
Office Action Response dated Oct. 18, 2007 from U.S. Appl. No. 10/821,206, 17 pages.
Office Action dated May 18, 2007 from U.S. Appl. No. 10/821,206, 9 pages.
Notice of Allowance dated Jan. 3, 2007 from U.S. Appl. No. 10/804,471, 7 pages.
Office Action Response dated Nov. 7, 2006 from U.S. Appl. No. 10/804,471, 14 pages.
Office Action dated Aug. 7, 2006 from U.S. Appl. No. 10/804,471, 9 pages.
Notice of Allowance dated Dec. 11, 2009 from U.S. Appl. No. 11/803,548, 6 pages.
Office Action Response dated Oct. 20, 2009 from U.S. Appl. No. 11/803,548, 10 pages.
Office Action dated Aug. 27, 2009 from U.S. Appl. No. 11/803,548, 9 pages.
Notice of Allowance dated Jul. 12, 2007 from U.S. Appl. No. 10/817,749, 8 pages.
Office Action Response dated May 21, 2007 from U.S. Appl. No. 10/817,749, 16 pages.
Office Action dated Mar. 20, 2007 from U.S. Appl. No. 10/817,749, 22 pages.
Office Action Response dated Oct. 10, 2006 from U.S. Appl. No. 10/817,749, 23 pages.
Office Action dated May 9, 2006 from U.S. Appl. No. 10/817,749, 16 pages.
International Preliminary Report on Patentability dated Oct. 27, 2005 from PCT Application No. PCT/US04/10917, 13 pages.
International Search Report and Written Opinion dated Nov. 23, 2004 from PCT Application No. PCT/US04/10917, 23 pages.
Office Action dated Mar. 17, 2009 from Japanese Application No. 2006-509836, 6 pages.
Office Action Response dated Sep. 16, 2009 from Japanese Application No. 2006-509836, 13 pages.
Notice of Allowance dated May 11, 2010 from Japanese Application No. 2006-509836, 2 pages.

Notice of Allowance dated Sep. 28, 2010 from U.S. Appl. No. 10/784,478, 6 pages.
Office Action dated Aug. 4, 2010 from U.S. Appl. No. 11/975,040, 19 pages.

Office Action Response dated Oct. 26, 2010 from U.S. Appl. No. 11/975,040, 10 pages.

* cited by examiner

FIG. 6

| Filter Name | Input Impedance |
|---|---|
| F1 | 2.0 Meg Ohm |
| F2 | 985.3K Ohm |
| F3 | 88.0K Ohm |
| F4 | 45.0K Ohm |

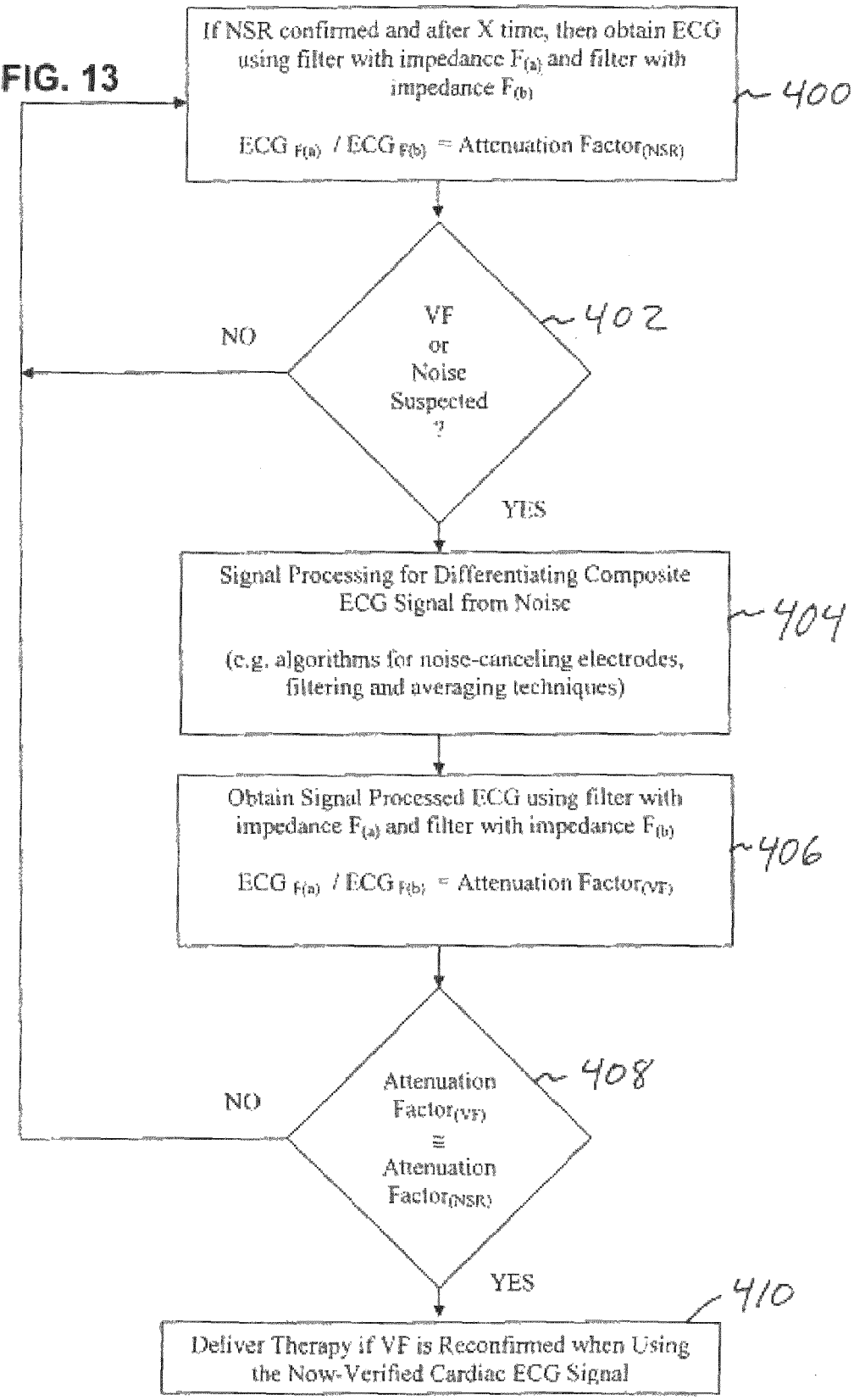

BIOPOTENTIAL SIGNAL SOURCE SEPARATION USING SOURCE IMPEDANCES

RELATED APPLICATIONS

This application is a continuation of U.S. patent application Ser. No. 10/821,206 filed on Apr. 8, 2004, to issue as U.S. Pat. No. 7,555,335 on Jun. 30, 2009, which claims the benefit of Provisional Patent Application Ser. No. 60/462,272, filed on Apr. 11, 2003, to which Applicant claims priority under 35 U.S.C. §120 and 35 U.S.C. §119(e), respectively, and which are incorporated herein by reference in their entirety.

FIELD OF THE INVENTION

The present invention relates generally to implantable medical devices and, more particularly, to a method of separating biopotential signal sources having differences in source impedances.

BACKGROUND OF THE INVENTION

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and can be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia can quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical Implantable cardioverter/defibrillators (ICDs) include one or more endocardial leads to which at least one defibrillation electrode is connected. Such ICDs are capable of delivering high-energy shocks to the heart, interrupting the ventricular tachyarrhythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure.

SUMMARY OF THE INVENTION

The present invention is directed to cardiac monitoring and/or stimulation methods and systems that, in general, provide transthoracic monitoring, defibrillation therapies, pacing therapies, or a combination of these capabilities. Embodiments of the present invention include cardiac methods and devices that separate signals using at least two composite signals acquired at at least two input impedances. A target source impedance may be selected, and a cardiac signal may be separated from composite signals using the selected target source impedance.

A medical system of the present invention includes a cardiac device having a housing that provides amplification circuitry configured to have a first amplifier input impedance and a second amplifier input impedance, such as by using two separate circuits or channels, or by using a common circuit or channel and switching between two input impedances. One or more electrode assemblies are coupled to the amplification circuitry. A signal processor is provided in the housing and configured to separate a source signal using a first composite signal detected at the first input impedance and a second composite signal detected at the second input impedance.

In one configuration, the first and second amplifiers each include a sample and hold amplifier, outputs of which are respectively coupled to a multiplexer. Outputs of the multiplexer are coupled the signal processor. The signal processor samples the first and second composite signals substantially synchronously in this configuration. In the case of sensing by use of intracardiac electrodes, the signal processor may sample the first and second composite signals substantially synchronously at a sampling frequency greater than about 400 Hz. In the case of sensing by use of subcutaneous, non-intracardiac electrodes, the signal processor samples the first and second composite signals substantially synchronously at a sampling frequency greater than about 50 Hz.

According to one embodiment of the invention, a medical system includes a cardiac monitoring device having a housing that provides amplification circuitry configured to have a first amplifier input and a second amplifier input. The first amplifier input has a first input impedance and the second amplifier input has a second input impedance different from the first input impedance. A first electrode assembly is coupled to the first amplifier input and a second electrode assembly is coupled to the second amplifier input. A signal processor is also provided in the housing and coupled to the amplification circuitry. The signal processor is configured to separate a source signal using a first composite signal detected at the first input impedance and a second composite signal detected at the second input impedance.

The first input impedance may be adjustable relative to the second input impedance. The first input may include a first input amplifier circuit and the second input may include a second input amplifier circuit. In one implementation, the amplification circuitry includes a first channel associated with the first input impedance and a second channel associated with the second input impedance. The phase response of the first input amplifier circuit is preferably about equal to that of the second input amplifier circuit.

The first electrode assembly and the second electrode assembly may be closely spaced (e.g., 2 cm or less), and may include one or more leads coupled to the housing, wherein the first and second electrode assemblies may be located on the leads. In one embodiment, the first electrode assembly includes at least one bipolar electrode arrangement. In other embodiments, the housing may include one or more of the electrode arrangements. In a subcutaneous system, the first electrode assembly may include at least one electrode arrangement configured for subcutaneous placement in a patient. The electrode arrangement may include an electrode array configured for subcutaneous placement in a patient. In another embodiment, a patient-external system implementation may employ at least one surface electrode arrangement.

In other embodiments, the amplification circuitry may be configured to have a first input impedance and a second input impedance, and include a switch configured to switch the amplification circuitry between the first and second input impedances. An electrode arrangement is coupled to the amplification circuitry, and a signal processor is coupled to the amplification circuitry. The signal processor is configured to separate a cardiac signal using a first composite signal sensed at the first input impedance and a second composite signal sensed at the second input impedance. The first input impedance may be adjustable relative to the second input impedance.

In one configuration, the electrode arrangement comprises intracardiac electrodes, and the switch switches between the first and second input impedances at a frequency greater than about 800 Hz. In another configuration, the electrode arrangement comprises subcutaneous, non-intracardiac electrodes, and the switch switches between the first and second input impedances at a frequency greater than about 100 Hz. The signal processor may include a filter configured to filter the composite signal to remove frequencies associated with the switch. The signal processor may sample the first and second composite signals substantially synchronously at a time when the first and second composite signals are valid in order to remove frequencies associated with switching. In a further configuration, the switch switches between the first and second input impedances during a cardiac cycle. In another configuration, the switch switches from one of the first and second input impedances to the other of the first and second input impedances after a duration exceeding one or more cardiac cycles.

The first electrode assembly and the second electrode assembly may be unipolar, bipolar, or multipolar electrode arrangements separated by less than about 2 centimeters. The electrode arrangement may be included on a lead coupled to the housing, and configured for subcutaneous placement in a patient. In another embodiment the housing may include a housing or can electrode arrangement. The housing electrode arrangement may also include an indifferent electrode arrangement.

A method of signal separation in accordance with the present invention may involve receiving, at a first input impedance, a first composite signal from an electrode arrangement, and receiving, at a second input impedance, a second composite signal from the electrode arrangement. A target source impedance may be selected, and a cardiac signal may be separated from the first and second composite signals using the selected target source impedance.

In one embodiment, separating the cardiac signal involves use of an attenuation factor defined by a ratio of amplitudes of the first and second composite signals. The attenuation factor is preferably determined from sensed normal sinus rhythm beats. The attenuation factor may be updated periodically.

According to one arrhythmia detection approach using attenuation factors, a baseline attenuation factor is computed at a time of non-arrhythmia, such as during normal sinus rhythm. At a later time, a subsequent attenuation factor may be computed. The baseline attenuation factor is compared to the subsequent attenuation factor. A cardiac signal source may be confirmed based on the comparison, thus providing a means for discrimination between noise and a ventricular tachyarrhythmia.

In another embodiment, the second input impedance is selected to attenuate a target source signal to between about one-fourth to about three-fourths of the target source signal from the first composite signal. In another embodiment, the second input impedance is selected to attenuate a target source signal to a predefined fractional level of the target source signal from the first composite signal. In other embodiments, the cardiac signal may be separated using a linear combination of the first composite signal and the second composite signal.

The second composite signal may be received by an amplifier having two or more selectable discrete input impedances. A selected amplifier input impedance may be chosen such that it attenuates a target source signal from the second composite signal to between about one-fourth to about three-fourths of the target source signal from the first composite signal. In embodiments of the present invention, the electrode arrangement includes a first electrode assembly and a second electrode assembly, the first electrode assembly sensing the first composite signal at the first impedance, and the second electrode assembly sensing the second composite signal at the second impedance.

In other embodiments, the electrode arrangement includes an electrode arrangement and a switch, the switch selecting between the first and second input impedances. The method may further involve band-pass filtering or synchronously sampling the first and second composite signals to remove frequencies related to switching between the first input impedance and the second input impedances.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 6 is a chart illustrating various input impedances used to sense a composite signal useful for signal separation in accordance with the present invention;

FIG. 13 is a flow diagram of a cardiac signal source confirmation method and tachyarrhythmia detection approach in accordance with an embodiment of the present invention.

Figure 1:
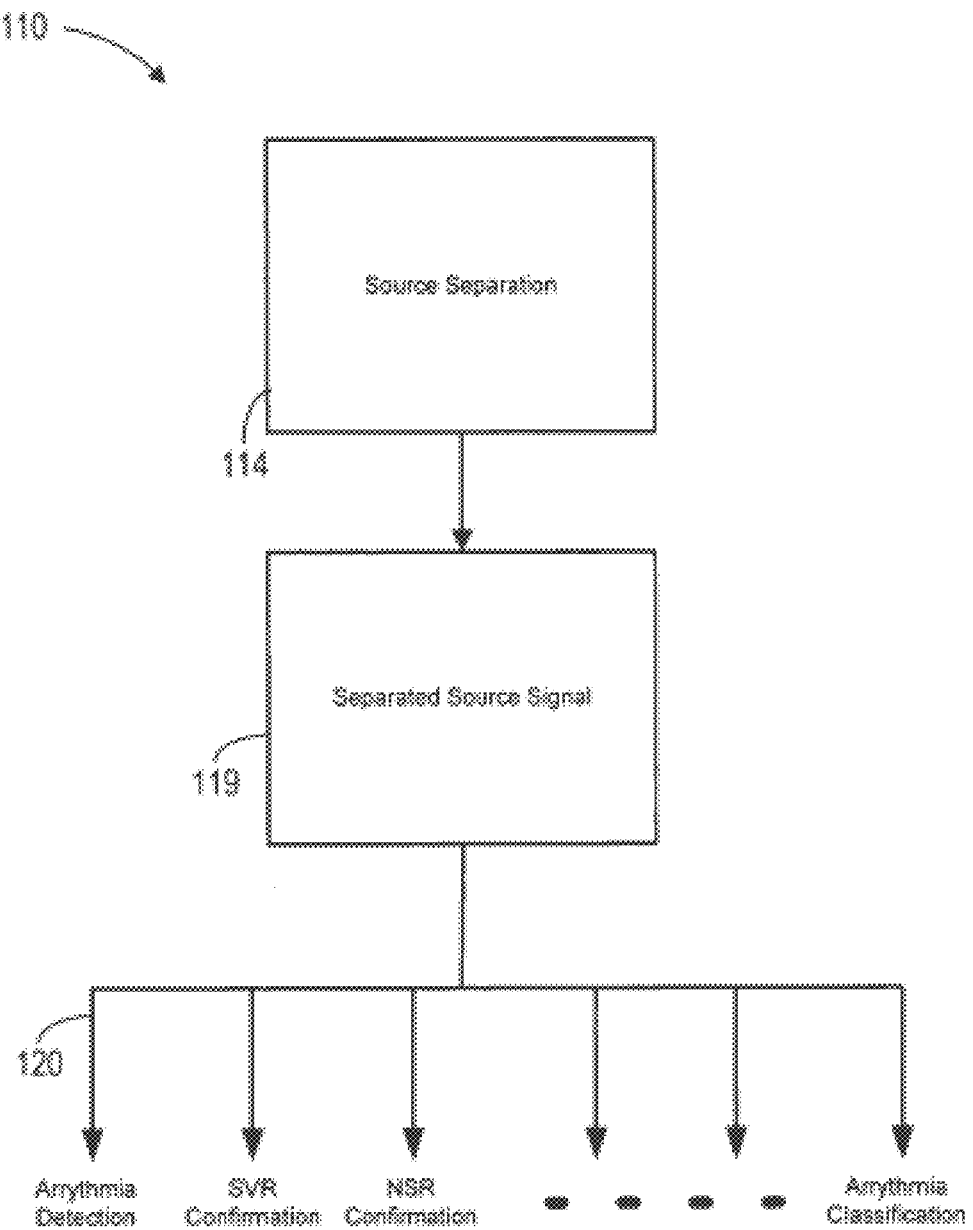
FIG. 1 is a block diagram illustrating uses of signal separation in accordance with the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A medical device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implantable, patient-external or partially implantable device need not include all of the features described herein, but may be implemented to include selected features that provide for useful structures and/or functionality. Such a device may be implemented to provide a variety of therapeutic or diagnostic functions.

In general terms, signal separation devices and methods in accordance with the present invention may be used with a subcutaneous cardiac monitoring and/or stimulation device. One such device is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

Certain cardiac device configurations contemplated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a cardiac device in accordance with the present invention, are disclosed in commonly owned U.S. Pat. Nos. 5,133,353; 5,179,945; 5,314,459; 5,318,597; 5,620,466; and 5,662,688, which are hereby incorporated herein by reference in their respective entireties.

An ITCS device employing signal separation in accordance with the present invention may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in this disclosure may be implemented in a wide range of medical devices, and that such embodiments and features are not limited to the particular devices described herein.

Examples of arrhythmia detection and discrimination circuitry, structures, and techniques, aspects of which may be implemented by a cardiac device in accordance with the present invention are disclosed in commonly owned U.S. Pat. Nos. 5,301,677 and 6,438,410, which are hereby incorporated herein by reference. Examples of pattern and rate-based arrhythmia detection and discrimination circuitry, structures, and techniques, aspects of which may be implemented by a cardiac device in accordance with the present invention are disclosed in U.S. Pat. Nos. 5,545,186; 5,855,593; 6,141,581; 6,259,947; and 6,487,443, which are hereby incorporated herein by reference.

In particular configurations, a cardiac device of the present invention may also perform functions traditionally performed by pacemakers, such as providing various pacing therapies as are known in the art. Examples of pacemaker circuitry, structures and functionality, aspects of which may be incorporated in a cardiac device in accordance with the present invention are disclosed in commonly owned U.S. Pat. Nos. 4,562,841; 5,036,849; 5,284,136; 5,376,106; 5,540,727; 5,836,987; 6,044,298; and 6,055,454, which are hereby incorporated herein by reference.

It is also understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Referring now to FIGS. 1 through 4, various illustrative cardiac sensing and/or stimulation devices and methods employing cardiac signal separation in accordance with the present invention are described. FIG. 1 illustrates a source separation methodology 110 in accordance with an embodiment of the present invention. A source separation process 114 is performed, providing a separated signal 119. The separated signal 119 is available for a variety of uses 120, such as arrhythmia detection, SVR (Supra-Ventricular Rhythm) confirmation, NSR (Normal Sinus Rhythm) confirmation, arrhythmia classification or other use.

Figure 2:
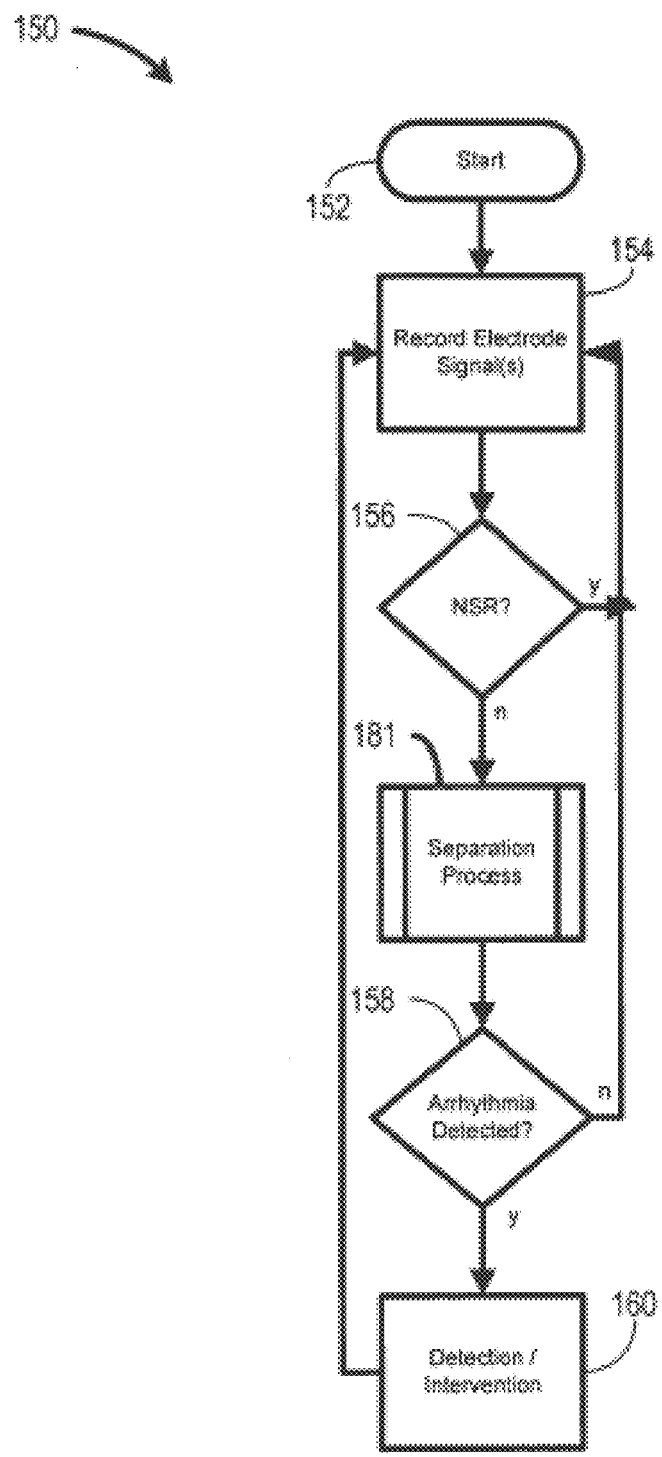
FIG. 2 is a block diagram of a cardiac sensing methodology incorporating signal separation in accordance with the present invention.

FIG. 2 illustrates a signal source separation methodology 150 as part of a cardiac arrhythmia detection approach in accordance with an embodiment of the present invention. After initiating 152 the methodology 150, a signal recording process 154 begins. During the signal recording process 154, one or more electrode signals are recorded for current or later processing, such as for signal source separation processing. The recording may be continuous or performed for a given period of time. At decision block 156, a determination is made as to the presence or absence of an NSR using techniques described herein or otherwise known in the art. If an NSR is detected, no other action is necessary, and recording and evaluation continues 154.

If NSR is absent, it is desirable to determine whether an adverse cardiac condition exists, which may necessitate intervention, or whether there is simply a spurious signal loss or other event not necessitating intervention. A loss of NSR detection at decision block 156 results in initiation of a signal separation process 181, such as that described below with regard to FIG. 3. After completion of the signal separation process 181, a separated cardiac signal is used to determine 158 if an arrhythmia is present, such as a ventricular tachycardia or ventricular fibrillation. A cardiac therapy is delivered 160 if a sustained arrhythmia is detected. If no arrhythmia is detected 158, a determination is made 160 as to whether other processing is necessary. If no further processing is necessary, the recording process 154 continues. If further processing is necessary, such additional processing 160 is performed, along with any further action associated with processing 160, after which the recording process 154 continues.

Figure 3:
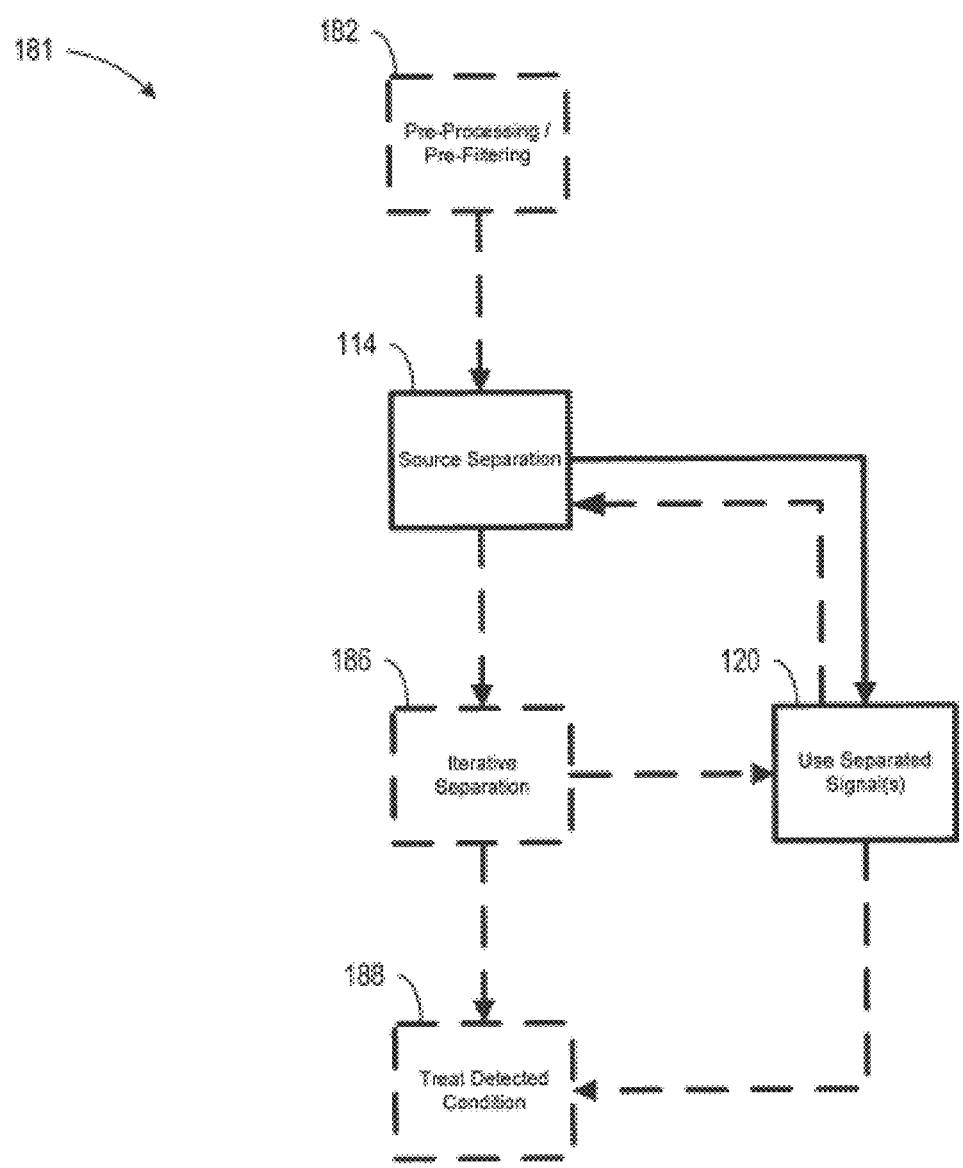
FIG. 3 is a block diagram of a signal separation process in accordance with the present invention.

FIG. 3 illustrates an embodiment of a signal source separation process 181 in accordance with the present invention. A set of composite signals, including at least two and up to n signals, are selected for separation, where n is an integer. In one embodiment, each of a number of different electrode pairs provides a composite signal associated with an unknown number of sources. In another embodiment, a selected electrode pair is switched between at least two input impedances, and a signal is recorded for each input impedance. In a configuration employing intracardiac electrodes, the switching between a first input impedance and a second input impedances may occur at a frequency greater than about 800 Hz. In a configuration employing subcutaneous, non-intracardiac electrodes, switching between the first and second input impedances may occur at a frequency greater than about 100 Hz.

Pre-processing and/or pre-filtering 182 may be performed on each of the composite signals. It may be advantageous to filter each composite signal using the same filtering function for multiple electrodes. Source separation 114 is performed, providing at least one separated signal. The separated signal may then be used 120 for some specified purpose, such as, for example, to confirm a normal sinus rhythm, determine a cardiac condition, define a noise signal, or other desired use.

If a treatment is indicated or desired, an appropriate treatment or therapy 188 is performed. If continued source separation is desired, the process returns to perform such source separation 114 and may iteratively separate 186 more signals until a desired signal is found, or all signals are separated.

Cardiac signals acquired by an ITCS system may be corrupted with a variety of noise content that cannot be removed by filtering alone. A noisy signal may cause oversensing and undesirable spurious shocks. If an initial loss of sinus rhythm occurs when sensing cardiac signals in a noisy environment, it is prudent to first verify and/or classify an arrhythmia prior to delivering a potentially unnecessary and painful therapy. Signal separation in accordance with the present invention may be used to separate the cardiac signal from a noisy composite signal, even in negative signal-to-noise ratio situations.

Figure 4A:
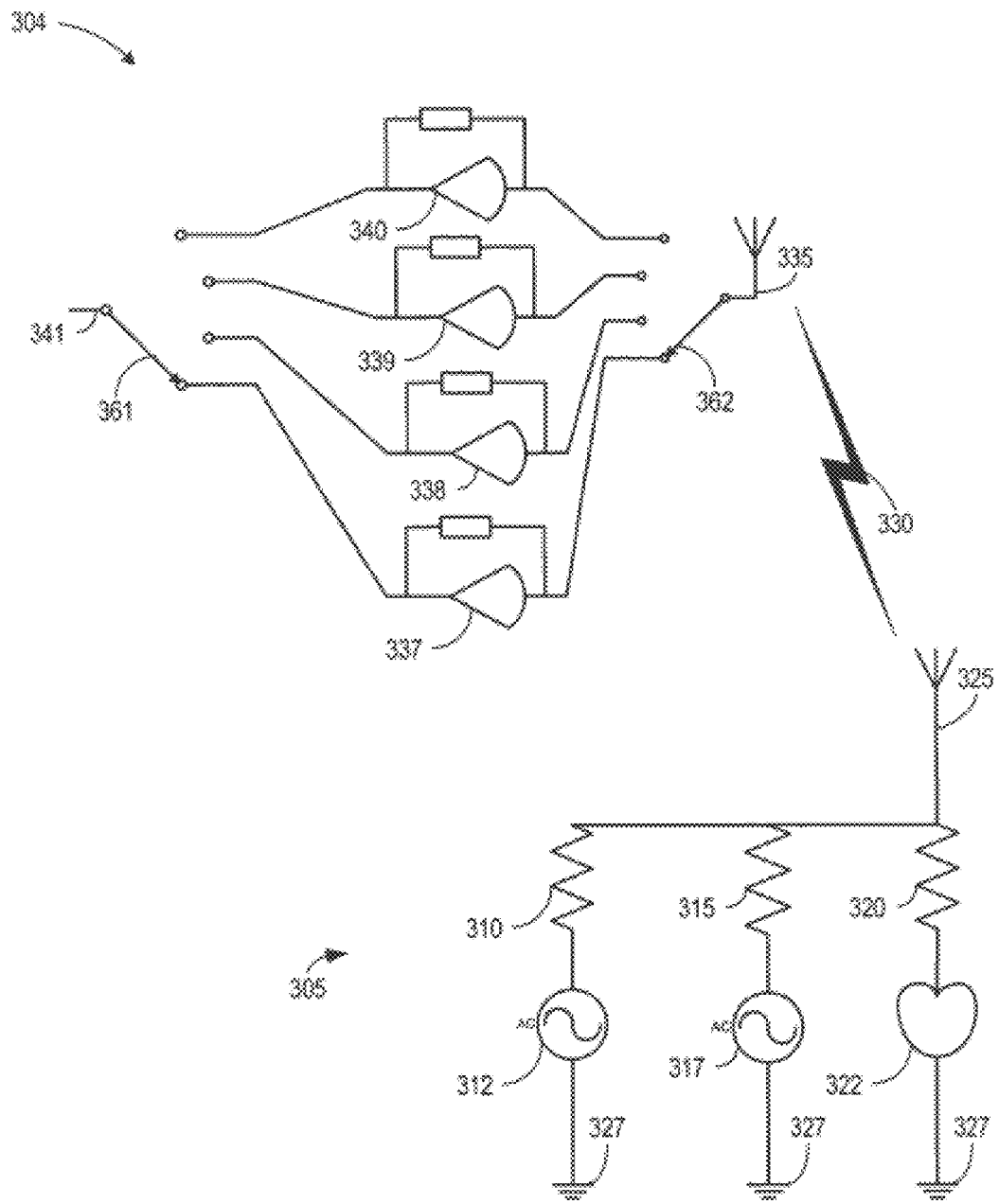
FIG. 4A is a diagram of sensing circuitry configured to provide signal sensing at multiple input impedances in accordance an embodiment of the present invention.
Figure 4B:
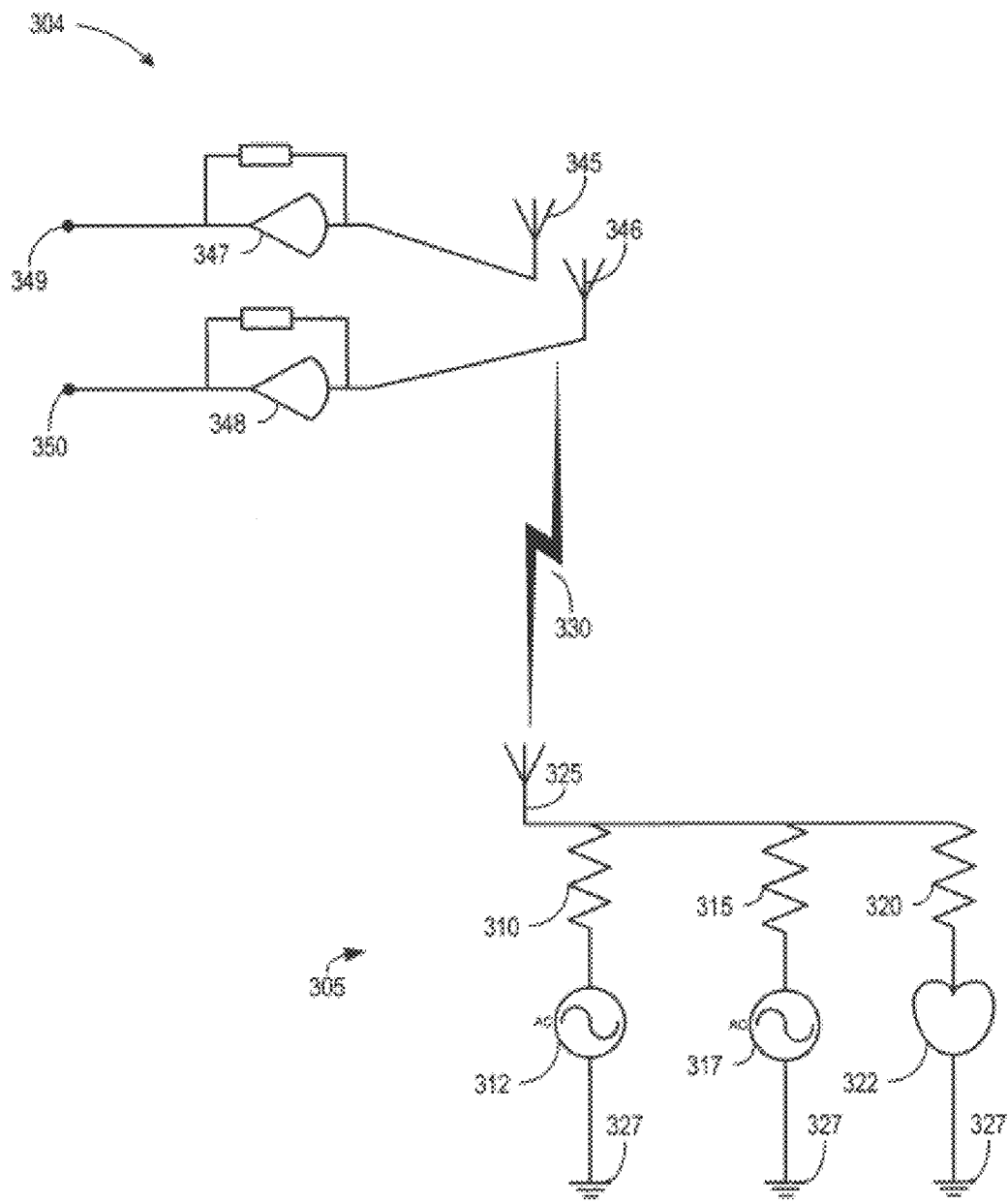
FIG. 4B is a diagram of sensing circuitry configured to provide signal sensing at multiple input impedances in accordance with another embodiment of the present invention.

In accordance with one embodiment of the present invention, a method for biopotential signal source separation is based on measured differences in source impedance. FIGS. 4A and 4B are diagrams of sensing circuitry 304 configured to provide signal sensing at multiple input impedances. Referring to FIG. 4A, a biopotential signal, such as the cardiac electrocardiogram (ECG), may be modeled as an in-series source voltage 322 and a cardiac source impedance 320 referenced to a ground 327. A first non-cardiac signal, such as a skeletal noise signal, may be modeled as an in-series source voltage 317 and a skeletal source impedance 315 referenced to the ground 327. A second non-cardiac signal, such as a noise signal of unknown origin, may be modeled as an in-series source voltage 312 and a noise source impedance 310 referenced to the ground 327.

A composite signal 330 may be composed of multiple signal sources (e.g. cardiac and skeletal muscles, or maternal and fetal ECGs) modeled as a parallel connection 305 of the individual sources 312, 317, and 322. If the source impedances 310, 315, and 320 are significantly different, and electrode interface impedance is small in comparison, the sensing circuitry 304 impedance may be adjusted to selectively attenuate a target signal at a given source impedance.

An ITCS device may be implemented to include a biopotential amplifier that collects identical, or nearly identical, biopotential signals at different input impedances. This may be accomplished, for example, with multiple channels of parallel, closely spaced bipolar leads, each amplified with different input impedances as will be illustrated in FIG. 4B, or with a single channel amplifier that rapidly switches between two or more input impedance stages as is illustrated in FIG. 4A.

In the implementation illustrated in FIG. 4A, involving rapid switching between input impedance stages, the signal is band-limited (passively filtered) to avoid aliasing that may occur as a result of switching/sampling. The switching may occur at a frequency much higher than any characteristic frequency of the constituent biopotential signals, so that the input signal may be assumed approximately constant across samples from the same switching/sampling cycle.

Two or more input impedance stages are designed such that the phase responses of the amplifier at each input impedance is nearly identical. Illustrated in FIG. 4A, a first amplifier 337 is provided at a first input impedance, a second amplifier 338 is provided at a second input impedance, a third amplifier 339 is provided at a third input impedance, and a fourth amplifier 340 is provided at a fourth input impedance. An electrode 335 is connected to one of the amplifiers 337, 338, 339, 340 through a switch 362. A switch 361 provides an attenuated signal at a connection 341 which is provided to detection and/or noise reduction circuitry, as will be further described below.

Using sensing circuitry 304 with adjustable and/or selectable input impedances, an estimate of the source impedance may be used to separate the ECG signal from the composite of signal sources 305. The source impedance of the desired signal for separation is estimated by selecting a first sensing circuitry 304 input impedance that attenuates the desired signal amplitude to between about one-fourth to about three-fourths (e.g., by half) that of a second sensing circuitry 304 input impedance. Alternatively, the outputs of amplifiers 337, 338, 339, and 340 may be tied to connection 341 to the exclusion of switch 361.

Referring now to FIG. 4B, a diagram of sensing circuitry 304 configured to provide signal sensing at multiple input impedances in accordance with another embodiment of the present invention is illustrated. The embodiment illustrated in FIG. 4B shows the two closely spaced electrodes, 345 and 346, coupled to their respective individual amplifiers 347 and 348, where the input impedance of amplifier 347 is different from the input impedance of amplifier 348. Connectors 349 and 350 provide attenuated signals to detection and/or noise reduction circuitry, as will be further described below. The amplification circuitry in this and other embodiments may be implemented to include separate channels each associated with a different input impedance, such as a first channel associated with a first input impedance and a second channel associated with a second input impedance.

The following example illustrates various aspects of an embodiment that provides for signal separation using source impedances with reference to FIGS. 5 through 9. In accordance with this illustrative example, two sensing input impedances are selected such that the amplitude of a target signal is attenuated by one-half for purposes of separating the target signal from a composite signal. The differentially attenuated signals may be combined to remove the target signal from the composite signal. If an estimate of the source impedance of the desired signal is available, the amplifier input impedance may be automatically controlled and amplifier output signals combined so as to have continuous extraction of the desired signal.

A signal separation method of the present invention may be expressed mathematically as follows:

If $s$ = desired signal, $n$ = noise, $\frac{1}{a}$ = attenuation factor of the target signal, and $k$ = unknown attenuation factor, but $\frac{1}{a} < k \leq 1$:

$$input_1 = s + n$$

$$input_2 = \frac{1}{a}s + kn$$

$$input_1 - a * input_2 = n - akn = (1-ak)n$$

$$s = input_1 - \frac{1}{(1-ak)}(input_1 - a * input_2)$$

$$= \left(1 - \frac{1}{1-ak}\right)input_1 - \frac{1}{1-ak}input_2$$

The above equations demonstrate that the desired signal, s, may be separated from the composite signals, $input_1$ and $input_2$, by measuring a value of k when the target signal in the composite signal $input_2$ is attenuated by a factor 1/a with respect to the target signal in the composite signal $input_1$.

Figure 4C:
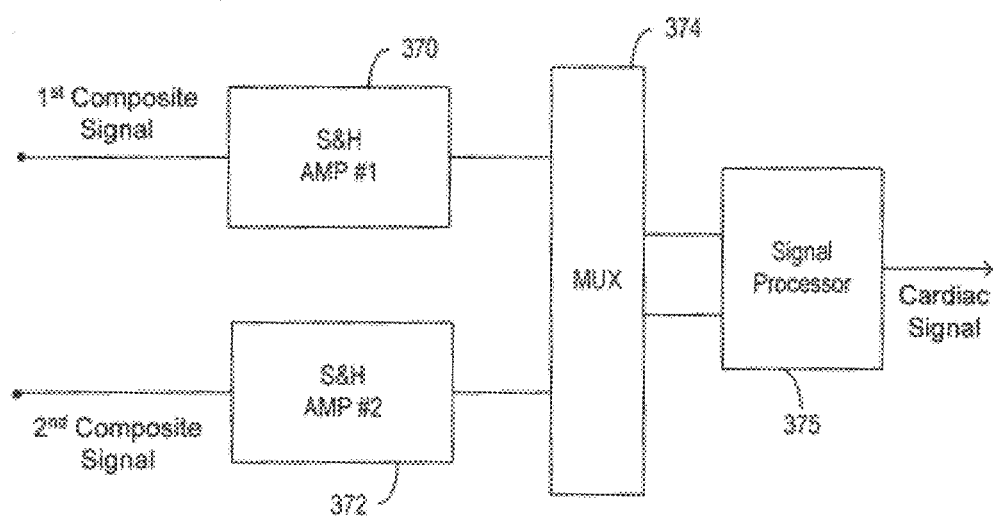
FIG. 4C is a diagram of sensing circuitry configured to provide signal sensing at multiple input impedances in accordance with a further embodiment of the present invention.

FIG. 4C is a diagram of sensing circuitry configured to provide signal sensing at multiple input impedances in accordance with a further embodiment of the present invention. According to this embodiment, a first composite signal is received by a first sample and hold amplifier 370 having a first input impedance and a second composite signal is received by a second sample and hold amplifier 372 having a second input impedance that attenuates the target signal of interest to between about ¼ and ¾ that of the first composite signal. Outputs of the first and second sample and hold amplifiers 370, 372 are coupled to respective inputs of a multiplexer 374. A signal processor 375 is coupled to outputs of the multiplexer 374.

In this configuration, the sample and hold amplifiers 370 and 372 sample the first and second composite signals substantially synchronously. In the case of sensing by use of intracardiac electrodes, sample and hold amplifiers 370, 372 may sample the first and second composite signals substantially synchronously at a sampling frequency greater than about 400 Hz. In the case of sensing by use of subcutaneous, non-intracardiac electrodes, sample and hold amplifiers 370, 372 may sample the first and second composite signals substantially synchronously at a sampling frequency greater than about 50 Hz.

Figure 5:
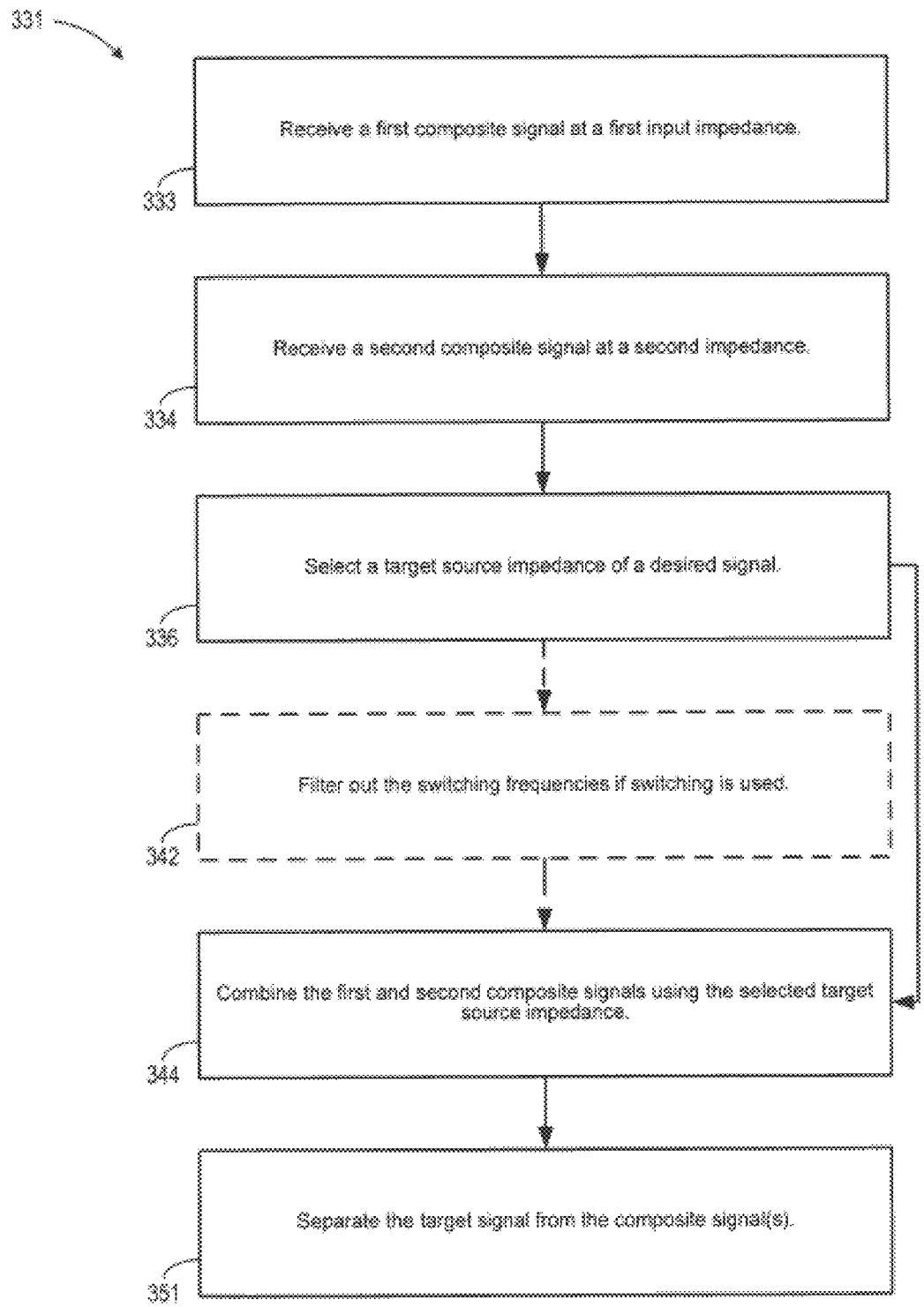
FIG. 5 is a flowchart depicting a cardiac signal separation method in accordance with the present invention.

FIG. 5 is a flow chart of a method of signal separation 331 in accordance with the present invention. According to this signal separation method 331, a first composite signal is received 333 at a first input impedance. A second composite signal is received 334 at an impedance different from the first input impedance. A target source impedance is selected 336. Typical source impedances may range between about 50K Ohms and about 80K Ohms. If a switched system is employed, such as that illustrated in FIG. 4A, the first and second composite signals may be filtered 342 or synchronously sampled to remove content associated with the switching frequencies from these signals. For example, the first and second composite signals may be sampled substantially synchronously at a time when the first and second composite signals are valid in order to remove frequencies associated switching. A combination 344 of the first and second composite signals is made, using the selected target source impedance. The target signal is separated 351 from the first and second composite signals and made available for use, such as for rhythm detection, identification, and/or verification.

FIGS. 6 through 9 facilitate a discussion of illustrative methods and devices for signal separation in accordance with embodiments of the present invention. FIG. 6 is a chart illustrating various input impedances used to sense a composite signal useful for signal separation in accordance with the present invention. In this illustrative example, four filters, F1-F4, having similar phase responses but different input impedances, are used to sense a composite signal. A first filter, F1, provides an input impedance of about 2.0M Ohms. A second filter, F2, provides an input impedance of about 958.3K Ohms. A third filter, F3, provides an input impedance of about 88.0K Ohms. A fourth filter, F4, provides an input impedance of about 45.0K Ohms.

Figure 7:
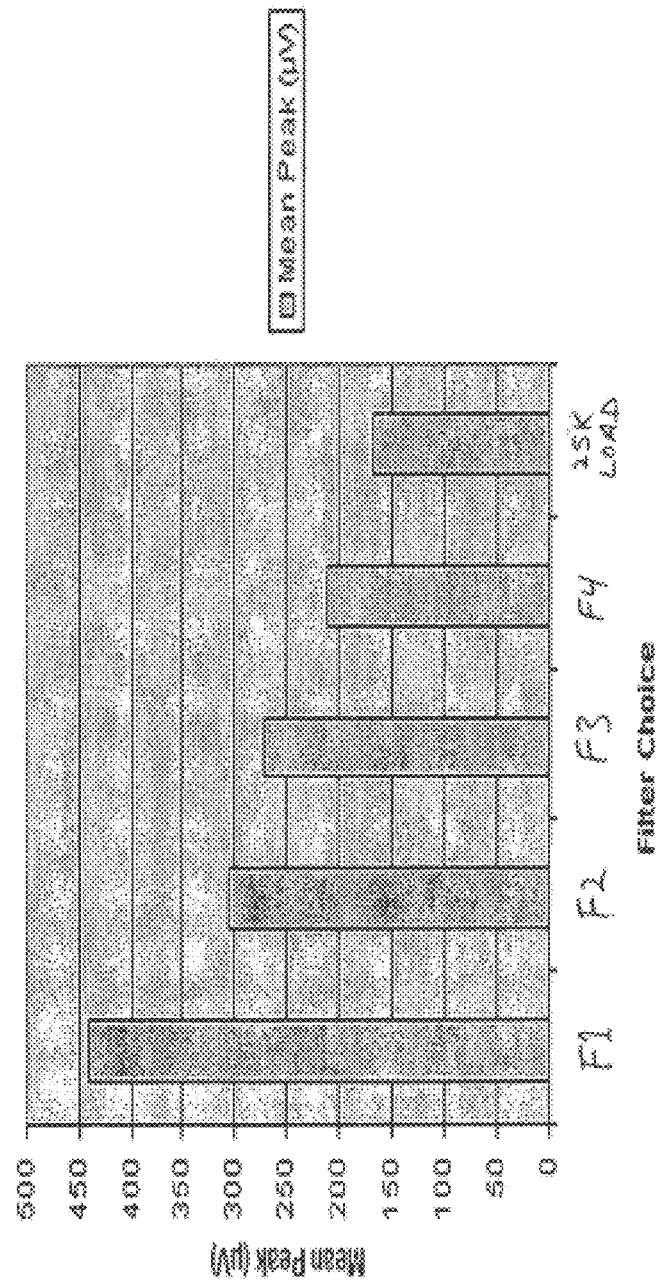
FIG. 7 is a bar graph illustrating mean peak sensed signal amplitude attenuation versus filter impedance loading, which may be used as guide for varying the input impedance in connection with sensing a composite signal useful for signal separation in accordance with the present invention.

FIG. 7 is a bar graph illustrating mean peak sensed signal amplitude versus the selection of filter (F1-F4), as described in FIG. 6, used to vary the input impedance. FIG. 7 illustrates signal attenuation associated with each of the selected filter impedances shown in FIG. 6. The mean peak signal amplitude (in microvolts) is shown on the ordinate of the graph, and the filter name is shown on the abscissa of the graph. As is evident from the graph, an input impedance of about 2M Ohms provides a composite signal having a mean peak cardiac signal of about 450 microvolts. Mean peak signal amplitude is seen to decrease with decreasing input impedance values, down to a mean peak value of about 160 microvolts at an input impedance of about 25K Ohm.

Figure 8:
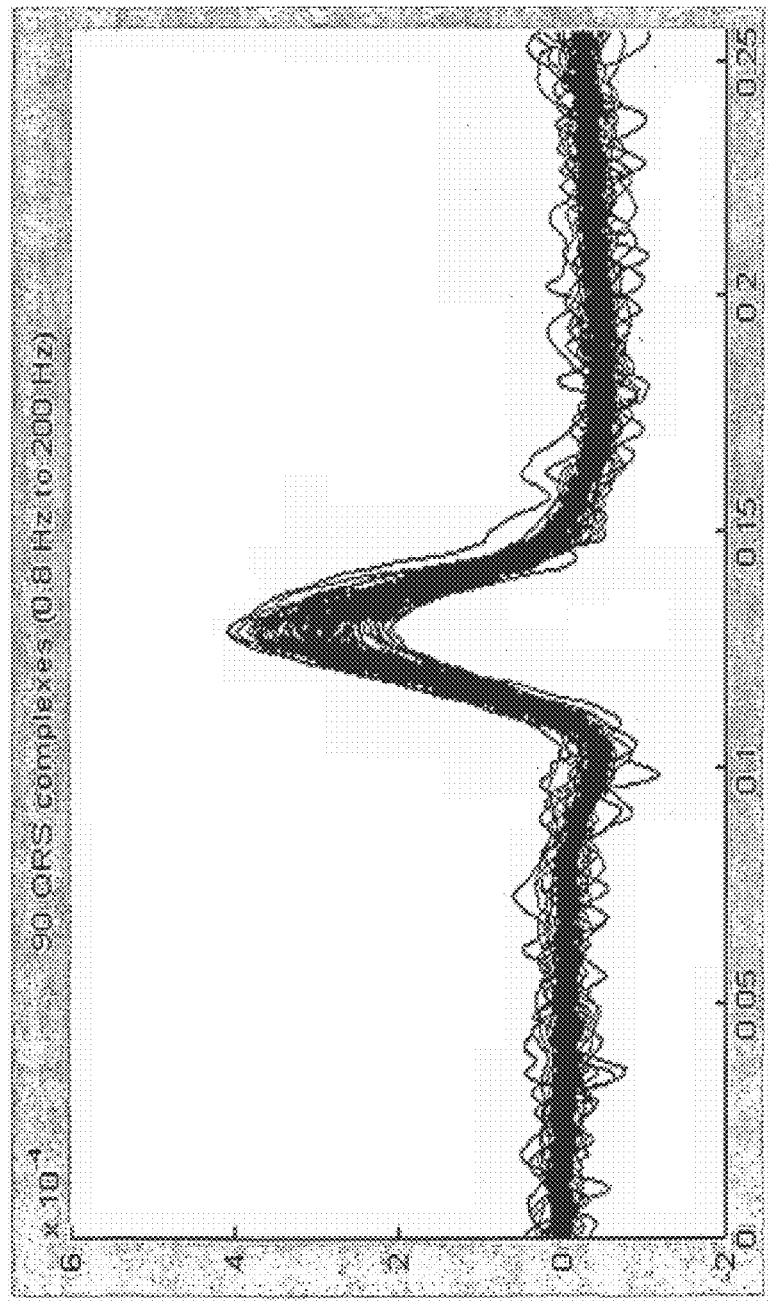
FIG. 8 is an overlay plot of signals sensed using the 958K Ohm input impedance filter designated filter F2 in FIGS. 6 and 7.

FIG. 8 is an overlay plot of signals sensed using the 958K Ohm input impedance filter, F2, shown in FIGS. 6 and 7. The signals plotted in FIG. 8 represent 90 sensed complexes. The mean peak signal amplitude (in volts) is shown on the ordinate of the graph, and time (in milliseconds) is shown on the abscissa of the graph.

Figure 9:
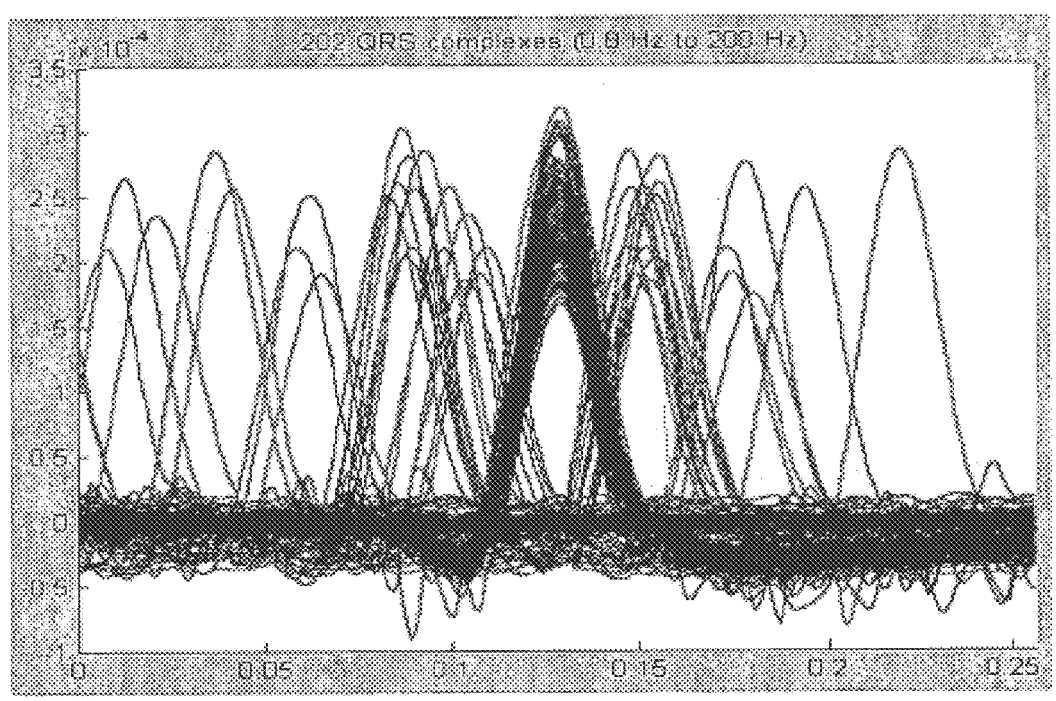
FIG. 9 is an overlay plot of signals sensed using the 45K Ohm input impedance filter designated filter F4 in FIGS. 6 and 7.

FIG. 9 is an overlay plot of signals sensed using the 45K Ohm input impedance filter, F4, shown in FIGS. 6 and 7. The signals plotted in FIG. 9 represent 202 complexes. The mean peak signal amplitude (in volts) is shown on the ordinate of the graph, and time (in milliseconds) is shown on the abscissa of the graph. Also evident is a noise component, which is significantly more prominent in FIG. 9 than is seen in the plot of FIG. 8. It can also be seen that the amplitude of the peak in the overlay plot of FIG. 9 is reduced appreciably relative to the peak of the plot in FIG. 8, such attenuation typically ranging between about one-fourth to about three-fourths the amplitude value of the peak of the plot in FIG. 8. Using the two composite signals illustrated in FIGS. 8 and 9, a signal separation method, such as the method illustrated in FIG. 5, may be performed.

The signal samples used to produce the plots shown in FIGS. 8 and 9 are preferably processed by an R-wave detection algorithm in which the peaks of the QRS complexes are aligned and plotted one over the other. Input impedances that result in high cardiac signal-to-noise ratios produce consistent overlay plots, such as that shown in FIG. 8. Input impedances that result in low cardiac signal-to-noise ratios produce inconsistent overlay plots, such as that shown in FIG. 9. FIGS. 8 and 9 demonstrate that a biopotential source separation method using measured differences in source impedance can provide for selective attenuation of far field cardiac signals versus near field myopotentials.

The relative consistency of the overlay plots shown in FIGS. 8 and 9 may also be used for distinguishing between noise and arrhythmias, and, as such, may be used for arrhythmia detection. For example, obtaining one relatively consistent overlay plot and one relatively inconsistent overlay plot indicates the presence of noise. A comparison of the two overlay plots in this illustrative case would indicate the absence or non-detection of an arrhythmia. By way of further example, obtaining two relatively inconsistent overlay plots indicates the presence of an arrhythmia. A comparison of the two overlay plots in this example would indicate the presence or detection of an arrhythmia. Various known mathematical or pattern matching techniques may be used to perform a comparison (data or graphical patterns) of overlay plots as part of an arrhythmia detection and/or confirmation process.

A method of distinguishing and separating biopotential signals on the basis of differences in source impedance according to the present invention may aid in diagnosis and therapy decisions that rely on measurements from individual biopotential sources when multiple sources are present and not easily distinguishable. Such a method may also be used to determine whether multiple signals of different source impedances are present in a signal of unknown morphology.

A biopotential source separation method of the present invention may be used to distinguish and separate near field cardiac signals from far field biopotential signals in an intravenous cardiac rhythm management (CRM) system that attenuates far field myopotential signals. The method may also be used to create a correction signal from which myopotential or other signals may be subtracted from heart signals in a subcutaneous system in which the cardiac signal is far field and the myopotential signal is near field. This approach may further aid in noise detection when several sources with different source impedances are present. Near field signals are accentuated over far field signals if low input impedance signal acquisition circuits are used.

Additional aspects of methods in accordance with the present invention include demonstration of selective attenuation of far field cardiac signal versus near field myopotentials. This provides the opportunity for creation of a signal indicating the presence of myopotential signals. Methods in accordance with the present invention provide the opportunity for separation of cardiac signals from myopotential signals by combining signals from amplifiers with different input impedances.

According to another embodiment of the present invention, and with reference to FIG. 13, filters having differing input impedances may be used for tachyarrhythmia detection and/or discrimination. In the tachyarrhythmia detection approach depicted in FIG. 13, a baseline attenuation factor ($AF_{(NSR)}$) is computed 400 at a time of non-arrhythmia, such as during normal sinus rhythm (NSR). If NSR is confirmed, electrocardiograms (ECG) are obtained using a first filter, $F_{(a)}$, and a second filter, $F_{(b)}$, where the input impedances of the two filters are substantially different. The baseline attenuation factor, $AF_{(NSR)}$, is computed as the ratio $ECG_{F(a)}/ECG_{F(b)}$.

If an arrhythmia or noise is detected 402, processing for differentiating the composite ECG signal from noise is initiated 404, from which a cardiac signal is extracted. Several techniques may be used to separate a cardiac signal from a composite signal, including those disclosed or incorporated herein and in commonly owned, co-pending U.S. patent application Ser. No. 10/738,608, filed Dec. 17, 2003, which is hereby incorporated herein by reference.

A signal processed ECG is obtained 406 using the first filter, $F_{(a)}$, and the second filter, $F_{(b)}$. A subsequent attenuation factor, $AF_{(VF)}$, may be computed as the ratio $ECG_{F(a)}/ECG_{F(b)}$. The two attenuation factors, $AF_{(NSR)}$ and $AF_{(VF)}$, are compared. If the two attenuation factors are about equal 408, then the cardiac signal has been properly identified or verified. Presence of the suspected tachyarrhythmia is reconfirmed 410 using the now-verified cardiac signal. Therapy may then be delivered if persistence of the tachyarrhythmia is reconfirmed using the verified cardiac signal. If the two attenuation factors are not substantially equal 408, then the cardiac signal has not been properly identified or verified (i.e., noise detected), and tachyarrhythmia therapy may be delayed or not delivered.

Signal separation systems and methods in accordance with the present invention, as stated previously, are useful with implantable cardiac devices such as subcutaneous ITCS devices. The following descriptions with respect to FIGS. 10 through 12 disclose, in greater detail, systems and devices that may implement signal separation techniques and components in accordance with the present invention.

Figure 10:
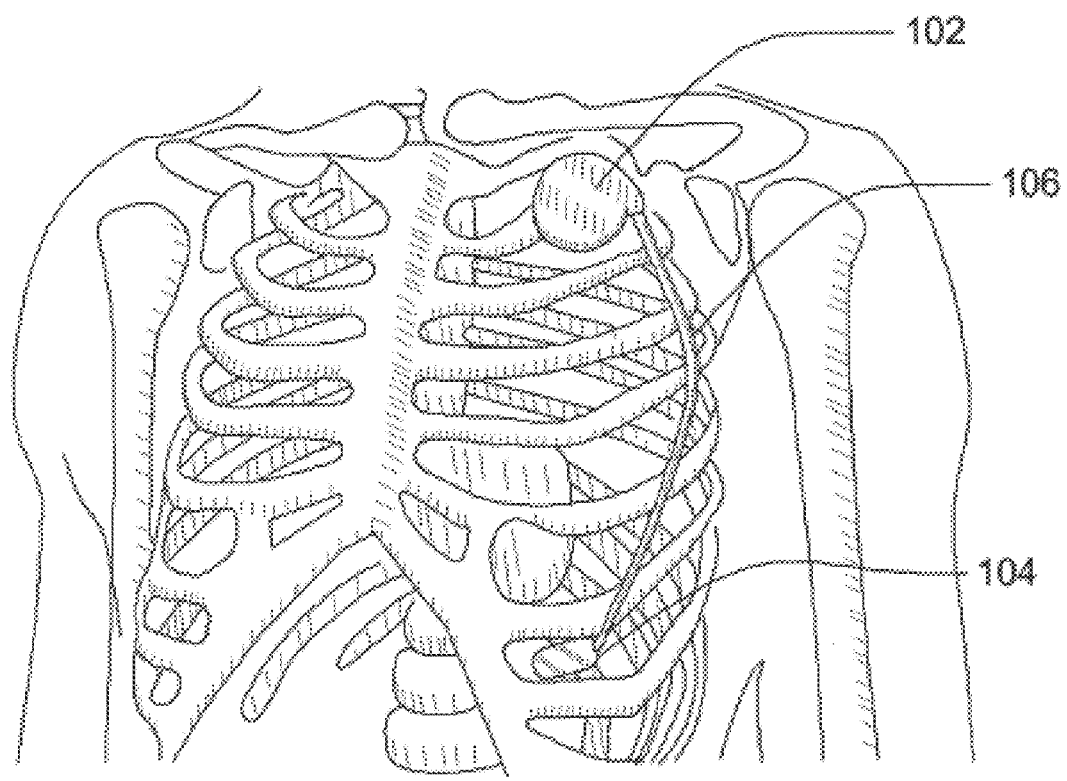
FIGS. 10 and 11 are views of a transthoracic cardiac sensing and/or stimulation device as implanted in a patient in accordance with an embodiment of the present invention.
Figure 11:
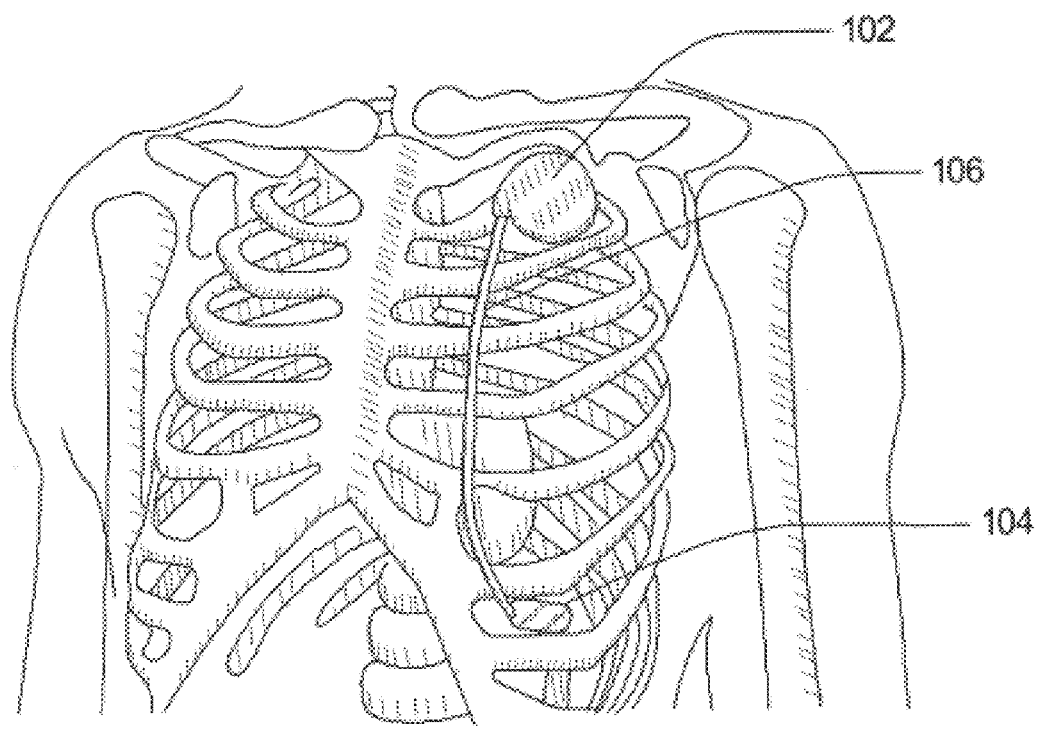

Referring now to FIGS. 10 and 11 of the drawings, there is shown a configuration of a transthoracic cardiac sensing and/or stimulation device having components implanted in the chest region of a patient at different locations. In the particular configuration shown in FIGS. 10 and 11, the ITCS device includes a housing 102 within which various cardiac sensing, detection, processing, and energy delivery circuitry may be housed.

Communications circuitry is disposed within the housing 102 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 10 and 11, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 10 and 11).

In one configuration, the lead assembly 106 is generally flexible and has a construction similar to conventional implantable, medical electrical leads (e.g., defibrillation leads or combined defibrillation/pacing leads). In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes a rigid or semi-rigid electrode support assembly, such as an elongated structure that positionally stabilizes the subcutaneous electrode 104 with respect to the housing 102. In this configuration, the rigidity of the elongated structure is sufficient to maintain a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and subcutaneous electrode 104 is provided in cases where the elongated structure is formed from an electrically conductive material, such as metal.

In one configuration, the electrode support assembly and the housing 102 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 102. The electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the electrode support assembly and housing 102. The header block arrangement may be provided on the housing 102 or the electrode support assembly. Alternatively, a mechanical/electrical coupler may be used to establish mechanical and electrical connections between the electrode support assembly and housing 102. In such a configuration, a variety of different electrode support assemblies of varying shapes, sizes, and electrode configurations may be made available for physically and electrically connecting to a standard ITCS device housing 102.

It is noted that the electrodes and the lead assembly 106 may be configured to assume a variety of shapes. For example, the lead assembly 106 may have a wedge, chevron, flattened oval, or a ribbon shape, and the subcutaneous electrode 104 may include a number of spaced electrodes, such as an array or band of electrodes. Moreover, two or more subcutaneous electrodes 104 may be mounted to multiple electrode support assemblies 106 to achieve a desired spaced relationship amongst subcutaneous electrodes 104.

An ITCS device may incorporate circuitry, structures and functionality of the subcutaneous implantable medical devices disclosed in commonly owned U.S. Pat. Nos. 5,203,348; 5,230,337; 5,360,442; 5,366,496; 5,391,200; 5,397,342; 5,545,202; 5,603,732; and 5,916,243, which are hereby incorporated herein by reference in their respective entireties.

Figure 12:
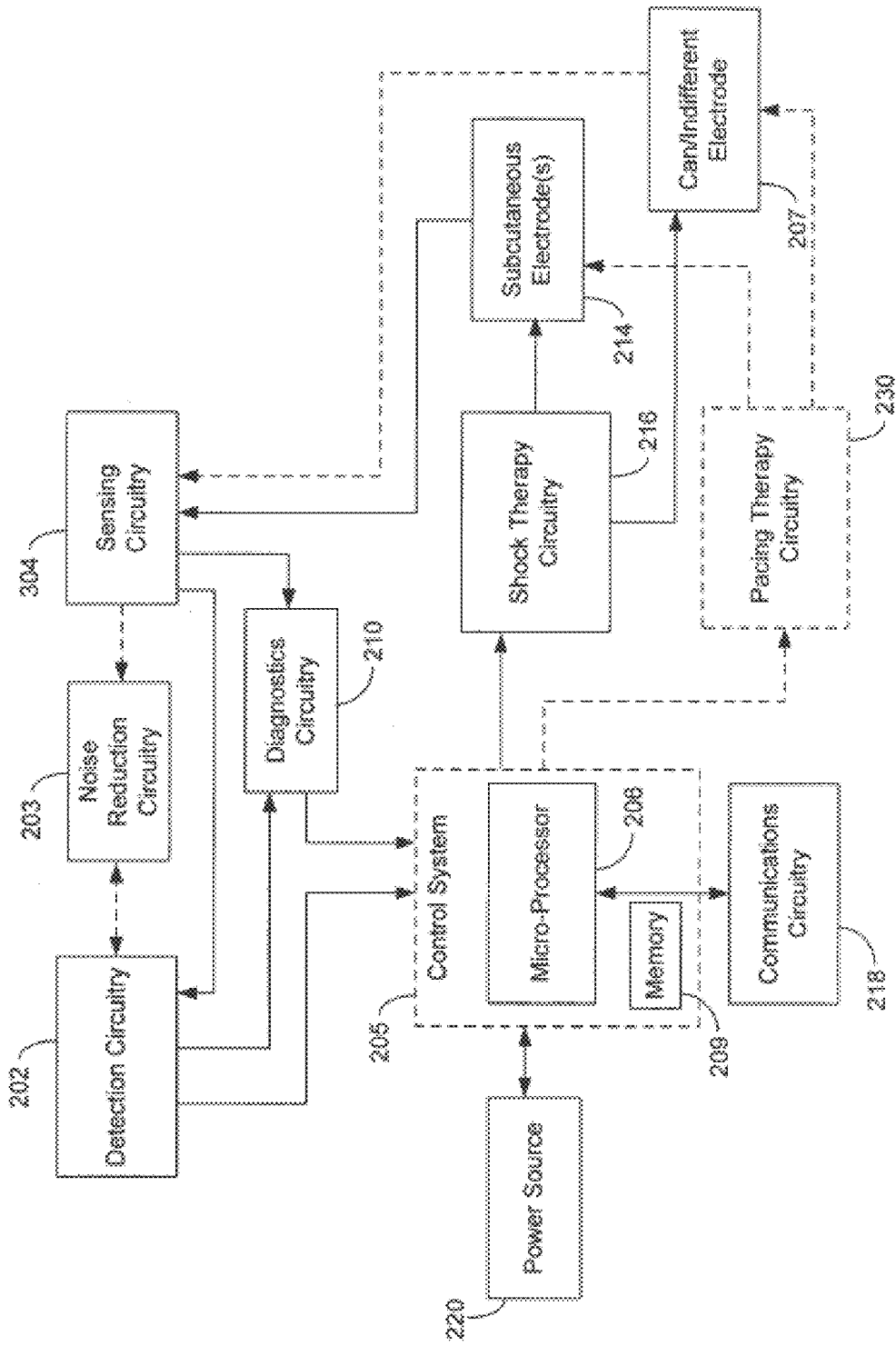
FIG. 12 is a block diagram illustrating various components of a transthoracic cardiac sensing and/or stimulation device in accordance with an embodiment of the present invention.

FIG. 12 is a block diagram depicting various components of an ITCS device in accordance with one configuration. According to this configuration, the ITCS device incorporates a processor-based control system 205 which includes a micro-processor 206 coupled to appropriate memory (volatile and non-volatile) 209, it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the subcutaneous electrode(s) 214 and the can or indifferent electrode 207 provided on the ITCS device housing. Cardiac signals may also be sensed using only the subcutaneous electrodes 214, such as in a non-active can configuration. Further, cardiac signals may be sensed using one or more surface electrodes, such as in a configuration in which the cardiac monitoring device is configured as a patient-external device. As such, unipolar, bipolar, or combined unipolar/bipolar electrode configurations as well as multi-element electrodes and combinations of electrodes may be employed.

The sensed cardiac signals are received by the sensing circuitry 304 (components of which are Illustrated in the embodiments of FIGS. 4A and 4B), which includes sense amplification circuitry and may also include a switch and filtering circuitry, as well as one or more analog-to-digital (A/D) converters. The sensed signals processed by the sensing circuitry 304 may be received by noise reduction circuitry 203, which may further reduce noise before signals are sent to the detection circuitry 202.

Noise reduction circuitry 203 may also be incorporated after detection circuitry 202 in cases where high power or computationally intensive noise reduction algorithms are required. The noise reduction circuitry 203, by way of amplifiers used to perform operations with the electrode signals, may also perform the function of the sensing circuitry 304. Combining the functions of sensing circuitry 304 and noise reduction circuitry 203 may be useful to minimize the necessary componentry and lower the power requirements of the system.

In the illustrative configuration shown in FIG. 12, the detection circuitry 202 is coupled to, or otherwise incorporates, noise reduction circuitry 203. The noise reduction circuitry 203 operates to improve the SNR of sensed cardiac signals by removing noise content of the sensed cardiac signals introduced from various sources. Typical types of transthoracic cardiac signal noise includes electrical noise and noise produced from skeletal muscles, for example. It is understood however, that signal separation systems and methods of the present invention are also useful for separating signals that may be of interest within what is considered as cardiac signal noise. For example, it may be desirable to separate and identify skeletal muscle signals. In the case of desired skeletal muscle signal separation, the cardiac signal would then be considered a noise signal.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode.

The detection circuitry 202 communicates cardiac signal information to the control system 205. Memory circuitry 209 of the control system 205 contains parameters for operating in various sensing, defibrillation, and, if applicable, pacing modes, and stores data indicative of cardiac signals received by the detection circuitry 202. The memory circuitry 209 may also be configured to store historical ECG and therapy data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 304. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Examples of ICD high energy delivery circuitry, structures, and functionality are disclosed in commonly owned U.S. Pat. Nos. 5,372,606; 5,411,525; 5,468,254; and 5,634,938, which are hereby incorporated herein by reference in their respective entireties.

In accordance with another configuration, an ITCS device may incorporate a cardiac pacing capability in addition to cardioversion and/or defibrillation capabilities. As is shown in dotted lines in FIG. 12, the ITCS device may include pacing therapy circuitry 230 coupled to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

A number of cardiac pacing therapies may be useful in a transthoracic cardiac monitoring and/or stimulation device. Such cardiac pacing therapies may be delivered via the pacing therapy circuitry 230 as shown in FIG. 12. Alternatively, cardiac pacing therapies may be delivered via the shock therapy circuitry 216, which effectively obviates the need for separate pacemaker circuitry.

The ITCS device shown in FIG. 12 may be configured to receive signals from one or more physiologic and/or non-physiologic sensors. Depending on the type of sensor employed, signals generated by the sensors may be communicated to transducer circuitry coupled directly to the detection circuitry 202 or indirectly via the sensing circuitry 304. It is noted that certain sensors may transmit sense data to the control system 205 without processing by the detection circuitry 202.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device via the communications circuitry 218. It is noted that physiologic or non-physiologic sensors equipped with wireless transmitters or transceivers may communicate with a receiving system external of the patient.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

The components, functionality, and structural configurations depicted in FIGS. 10-12 are intended to provide an understanding of various features and combination of features that may be incorporated in an ITCS device utilizing signal separation in accordance with the present invention. It is understood that a wide variety of ITCS and other implantable cardiac monitoring and/or stimulation device configurations are contemplated that may benefit from separation systems and methods of the present invention, ranging from relatively sophisticated to relatively simple designs. Moreover, it is contemplated that a patient-external cardiac monitoring and/or stimulation system employing surface electrodes and/or implantable subcutaneous electrodes may implement a biopotential signal separation methodology of the present invention. As such, particular ITCS or cardiac monitoring and/or stimulation device configurations may include particular features as described herein, while other such device configurations may exclude particular features described herein.

The ITCS device may detect a variety of physiological signals that may be used in connection with various diagnostic, therapeutic or monitoring implementations. For example, the ITCS device may include sensors or circuitry for detecting respiratory system signals, cardiac system signals, and signals related to patient activity. In one embodiment, the ITCS device senses intrathoracic impedance, from which various respiratory parameters may be derived, including, for example, respiratory tidal volume and minute ventilation. Sensors and associated circuitry may be incorporated in connection with an ITCS device for detecting one or more body movement or body position related signals. For example, accelerometers and GPS devices may be employed to detect patient activity, patient location, body orientation, or torso position.

The ITCS device may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

An ITCS device according to one approach provides an easy to implant therapeutic, diagnostic or monitoring system. The ITCS system may be implanted without the need for intravenous or intrathoracic access, providing a simpler, less invasive implant procedure and minimizing lead and surgical complications. In addition, this system would have advantages for use in patients for whom transvenous lead systems cause complications. Such complications include, but are not limited to, surgical complications, infection, insufficient vessel patentcy, complications associated with the presence of artificial valves, and limitations in pediatric patients due to patient growth, among others.

Various modifications and additions can be made to the various embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of signal separation, comprising:
receiving, at a first input impedance, a first composite signal from an electrode arrangement suitable for coupling to a heart;
receiving, at a second input impedance, a second composite signal from the electrode arrangement;
selecting a target source impedance; and
separating a cardiac source signal from another physiological source signal using the first and second composite signals and the selected target source impedance, the cardiac source signal having a first source impedance associated therewith and the another physiological source signal having a second source impedance associated therewith different from the first source impedance;
wherein the first input impedance is smaller than the first and second source impedances and the second input impedance is smaller than the first and second source impedances.

2. The method of claim 1, wherein the second input impedance is selected to attenuate a target source signal to between about one-fourth to about three-fourths of the target source signal from the first composite signal.

3. The method of claim 1, wherein the second input impedance is selected to attenuate a target source signal to a predefined fractional level of the target source signal from the first composite signal.

4. The method of claim 1, wherein the cardiac signal is separated using a linear combination of the first composite signal and the second composite signal.

5. The method of claim 1, wherein the second composite signal is received by an amplifier having a plurality of selectable discrete input impedances, and a selected amplifier input impedance attenuates a target source signal from the second composite signal to between about one-fourth to about three-fourths of the target source signal from the first composite signal.

6. The method of claim 1, wherein the electrode arrangement comprises a first electrode assembly and a second electrode assembly, the first electrode assembly sensing the first composite signal at the first impedance, and the second electrode assembly sensing the second composite signal at the second impedance.

7. The method of claim 6, wherein the first and second composite signals are sampled synchronously.

8. The method of claim 1, comprising selectably switching the electrode arrangement between the first input impedance and the second input impedance.

9. The method of claim 8, comprising band-pass filtering the first and second composite signals to remove frequencies related to the switching between the first input impedance and the second input impedance.

10. The method of claim 8, comprising sampling the first and second composite signals substantially synchronously at a time when the first and second composite signals are valid to remove frequencies associated the switching between the first input impedance and the second input impedance.

11. The method of claim 1, comprising performing cardiac rhythm detection using the separated cardiac signal.

12. The method of claim 1, comprising providing a cardiac monitoring and stimulation device configured to implement the signal separation method.

13. A method of signal separation, comprising:
receiving, at a first input impedance, a first composite signal from an electrode arrangement suitable for coupling to a heart;
receiving, at a second input impedance, a second composite signal from the electrode arrangement;
selecting a target source impedance; and
separating a cardiac source signal from another physiological source signal using the first and second composite signals and the selected target source impedance and using an attenuation factor, the cardiac source signal having a first source impedance associated therewith and the another physiological source signal having a second source impedance associated therewith different from the first source impedance;
wherein the first input impedance is smaller than the first and second source impedances and the second input impedance is smaller than the first and second source impedances.

14. The method of claim 13, wherein the attenuation factor is determined from sensed normal sinus rhythm beats.

15. The method of claim 14, wherein the attenuation factor is determined as a ratio of a first attenuation factor associated with the first input impedance and a second attenuation factor associated with the second input impedance different from the first input impedance.

16. The method of claim 13, wherein the attenuation factor is defined by a ratio of amplitudes of the first and the second composite signals.

17. The method of claim 13, wherein the attenuation factor is updated periodically.

18. The method of claim 13, comprising:
computing a subsequent attenuation factor;
comparing the attenuation factor to the subsequent attenuation factor; and
verifying that the separated cardiac signal represents a cardiac electrophysiological signal based on the comparison.

19. The method of claim 18, comprising discriminating between noise and the ventricular tachyarrhythmia based on the comparison.

20. The method of claim 13, wherein:
the electrode arrangement comprises a first electrode assembly and a second electrode assembly, the first electrode assembly sensing the first composite signal at the first impedance, and the second electrode assembly sensing the second composite signal at the second impedance; or
the electrode arrangement is coupled to a switch configured to selectably switch the electrode arrangement between the first input impedance and the second input impedance.

* * * * *